(12) United States Patent
Park et al.

(10) Patent No.: US 8,647,610 B2
(45) Date of Patent: Feb. 11, 2014

(54) USE OF MELANIN BIOSYNTHESIS INHIBITORS FROM KOREAN GINSENG AND THE COSMETIC COMPOSITION CONTAINING THEREOF FOR SKIN WHITENING

(75) Inventors: Jun Seong Park, Gyeonggi-do (KR); Hye Yoon Park, Gyeonggi-do (KR); Soo Mi Ahn, Gyeonggi-do (KR); Byung Young Kang, Seoul (KR); Jin Young Lee, Gyeonggi-do (KR); Eun Joo Kim, Gyeonggi-do (KR); Duck Hee Kim, Seoul (KR); Ih Seop Jang, Gyeonggi-do (KR)

(73) Assignee: Amorepacific Corporation, Seoul (KR)

( * ) Notice: Subject to any disclaimer, the term of this patent is extended or adjusted under 35 U.S.C. 154(b) by 536 days.

(21) Appl. No.: 12/740,212

(22) PCT Filed: Oct. 31, 2007

(86) PCT No.: PCT/KR2007/005454
§ 371 (c)(1),
(2), (4) Date: Jul. 26, 2010

(87) PCT Pub. No.: WO2009/057836
PCT Pub. Date: May 7, 2009

(65) Prior Publication Data
US 2010/0310485 A1 Dec. 9, 2010

(51) Int. Cl.
*A61K 8/00* (2006.01)
(52) U.S. Cl.
USPC .......................................................... 424/62
(58) Field of Classification Search
USPC .......................................................... 424/62
See application file for complete search history.

(56) References Cited

U.S. PATENT DOCUMENTS

| 2003/0175315 A1 | 9/2003 | Yoo et al. |
| 2006/0216261 A1 | 9/2006 | Yoo et al. |
| 2007/0098655 A1* | 5/2007 | Schmaus et al. ............... 424/62 |

FOREIGN PATENT DOCUMENTS

| CN | 1732010 A | 2/2006 |
| JP | 2003-212776 | 7/2003 |
| JP | 2005-289913 | 10/2005 |
| JP | 2006-124355 | 5/2006 |
| KR | 20050102571 | 10/2005 |
| WO | WO 2005/070436 | 8/2005 |

OTHER PUBLICATIONS

English translation of Guangchao Wang, Dermatosis and Cypridology, P500, Science Press (Jan. 31, 2002).
International Search Report for PCT/KR2007/005454, mailed Jul. 28, 2008.
Written Opinion for PCT/KR2007/005454, mailed Jul. 28, 2008.
Office Action and English translation dated Jun. 15, 2011 in CN 200780101086.5.
Guangchao Wang, "Dermatosis and Cypridology", P500, Science Press (Jan. 31, 2002).
Office Action and partial English translation in JP 2010-530909 dated Feb. 26, 2013.
Fox et al, "Transdermal Drug Delivery Enhancement . . . ", Molecules 2011, 16, 10507-10540.
Farwick et al, "Low Molecular Weight Hyaluronic Acid: Its Effects on Epidermal Gene Expression & Skin Ageing", SOFW Journal Nov. 2008.

* cited by examiner

*Primary Examiner* — Lezah Roberts
*Assistant Examiner* — Nannette Holloman
(74) *Attorney, Agent, or Firm* — Nixon & Vanderhye P.C.

(57) ABSTRACT

Disclosed herein is a whitening cosmetic composition containing plant-derived ginsenoside F1 (20-O-β-D-glucopyranosyl-20(S)-protopanaxatriol) as an active ingredient. More specifically, the ginsenoside F1 is obtained from particularly a ginseng extract using an acid, a base, an enzyme or microorganism, and a whitening cosmetic composition containing the ginsenoside F1 has an excellent effect of inhibiting melanin biosynthesis, and thus provides an excellent skin whitening effect.

2 Claims, No Drawings

USE OF MELANIN BIOSYNTHESIS INHIBITORS FROM KOREAN GINSENG AND THE COSMETIC COMPOSITION CONTAINING THEREOF FOR SKIN WHITENING

This application is the U.S. national phase of International Application No. PCT/KR2007/005454 filed 31 Oct. 2007 which designated the U.S., the entire contents of which is hereby incorporated by reference.

TECHNICAL FIELD

The present invention relates to a use of ginsenoside F1 obtained from a ginseng extract using an acid, a base, an enzyme or a microorganism producing the enzyme, and of a cosmetic composition containing the same, for skin whitening.

BACKGROUND ART

Various factors are involved in determining human skin color, and among them, factors, such as the activity of melanocytes, which make melanin pigments, the distribution of blood vessels, the thickness of the skin, and the presence or absence of pigments (e.g., carotenoid, bilirubin, etc.) in the human body, are of importance. The most important factor among them is black pigment melanin, which is produced by the action of various enzymes such as tyrosinase in human melanocytes. The formation of the melanin pigment is influenced by genetic factors, hormone secretion, physiological factors associated with stresses, and environmental factors such as UV light irradiation.

The melanin pigment, which is produced in melanin cells on the body skin, is a phenolic polymer having a complex of a black pigment and a protein. It blocks the sun's ultraviolet rays to protect the skin organs under the dermis and, at the same time, removes free radicals generated in skin tissues so as to protect proteins and genes in the skin. However, melanin, produced by internal or external stress stimuli in the skin, is a stable substance, which is not removed even when the stresses disappear, until it is discharged to the outside by skin keratinization. Thus, when melanin is produced in an unnecessarily large amount, hyperpigmentations, such as discoloration, freckles and spots, which are unfavorable in terms of beauty, will occur. As people who like outdoor activity have increased with an increase in leisure population, the need to prevent melanin pigmentation caused by UV light has increased. In order to satisfy this need, ascorbic acid, kojic acid, albutin, hydroquinone, glutathione, or derivatives thereof, or substances having tyrosinase inhibitory activity, have been used in cosmetics or medical drugs. However, the use thereof has been limited due to insufficient whitening effects and various problems, such as skin safety problems, and formulation and stability problems which occur when they are added to cosmetics.

DISCLOSURE

Technical Problem

Accordingly, the present inventors have conducted many studies to prepare whitening cosmetic composition which is derived from naturally occurring substances, is safe for the skin and, at the same time, has an excellent whitening effect and excellent product stability. As a result, the present inventors have found that ginsenoside F1 obtained by allowing plant extract, particularly ginseng extract, to react with an acid, an alkali or an enzyme, has an excellent effect of reducing melanin biosynthesis, thereby completing the present invention.

Therefore, it is an object of the present invention to examine the melanin biosynthesis inhibitory effect of ginsenoside F1 obtained by allowing plant extract to react with an acid, an alkali or an enzyme and to provide a cosmetic and therapeutic composition having an excellent whitening effect.

Technical Solution

The present invention provides ginsenoside F1 represented by the following formula 1 and the use of a cosmetic composition containing the same for skin whitening:

[Formula 1]

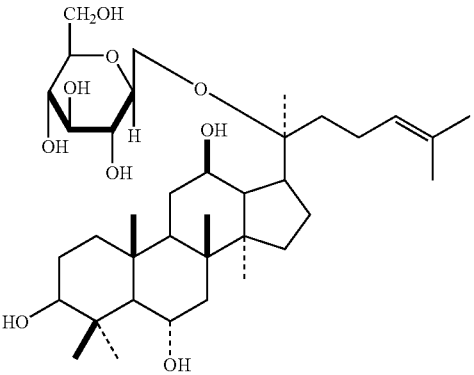

Hereinafter, the present invention will be described in detail.

The ginsenoside F1 is obtained from a plant extract. Particularly, the ginsenoside F1 which is contained in the cosmetic composition of the present invention is obtained from ginseng, red ginseng, white ginseng, fresh ginseng, ginseng tails, ginseng leaves or ginseng berries.

The extract that is used in the present invention may be prepared in the following manner. An organic solvent is added to a plant in an amount of about 1-6 times, and preferably about 3 times the weight of the plant, and the plant is defatted by extracting it 1-5 times at room temperature. An organic solvent is added to the defatted plant in an amount of about 1-8 times, and preferably about 4 times the weight of the defatted plant, and the defatted plant is extracted 1-5 times under reflux. The extract is incubated at 10-20° C. for 1-3 days, and then separated into residue and a filtrate through filtration and centrifugation. The separated filtrate is concentrated under reduced pressure, and the concentrate is suspended in water, and then treated with, for example, ethanol, to remove pigments therefrom. Then, the aqueous layer is extracted 1-5 times with an organic solvent, and then the obtained organic solvent layer is concentrated under reduced pressure to obtain an organic solvent extract. The organic solvent extract is dissolved in a small amount of methanol or the like, and then a large amount of ethyl acetate is added thereto. The produced precipitate is dried, thus obtaining the extract of the present invention. The organic solvent that is used in the present invention is preferably either a single solvent selected from the group consisting of anhydrous methanol, hydrated methanol, anhydrous ethanol and hydrated ethanol, or a mixed solvent of one of the above-mentioned methanols and one of the above-mentioned ethanols.

The extract is hydrolyzed using an acid, a base, an enzyme or a microorganism producing the enzyme, thus preparing ginsenoside F1.

When the acid is used, it may be either at least one acid selected from the group consisting of hydrochloric acid, sulfuric acid and nitric acid, or a mixture of said acid with at least one alcohol selected from the group consisting of ethanol, methanol and butanol. The alcohol that is used in the acid-alcohol mixture is preferably 50% ethanol. To the extract, either a 0.1-2N acid solution (preferably a 1N acid solution) or the acid-alcohol mixture, is added, and then the extract is hydrolyzed by heating under reflux in a water bath at a temperature of 50-100° C. (preferably 80° C.) for 0.5-2 hours.

When the base is used, it may be either at least one base selected from the group consisting of sodium hydroxide and potassium hydroxide, or a mixture of said base with at least one alcohol selected from the group consisting of ethanol, methanol and butanol. The alcohol that is used in the base-alcohol mixture is preferably 50% butanol. To the extract, either a 0.1-2N base solution, preferably a 1N base solution, or the base-alcohol mixture, is added, and then the extract is hydrolyzed by heating under reflux in a water bath at a temperature of 50-100° C. (preferably 100° C.) for 1-12 hours.

When the enzyme is used, it may be at least one selected from the group consisting of β-glucosidase, α,β-arabinosidase, α,β-rhamnosidase, β-glucuronidase, β-galactosidase and amyloglucosidase. The extract is dissolved in a 5-20-fold volume (preferably about 10-fold volume) of an acidic buffer solution, and then the enzyme is added thereto. Then, the extract is stirred in a water bath at about 37° C. for about 1-60 hours and, at the same time, the elimination rate of the substrate is examined by thin layer chromatography. When the substrate is completely eliminated, the extract is heated in hot water at 80-100° C. for 5-15 minutes. Then, the hydrolysis reaction is terminated and the reaction solution is collected.

When the microorganism is used, it may be a microorganism producing said enzyme. More specifically, the microorganism may be selected from the group consisting of *aspergillus* sp., *bacillus* sp., *penicillium* sp., *rhizopus* sp., *rhizomucor* sp., *talaromyces* sp., *bifidobacterium* sp., *mortierella* sp., *Cryptococcus* sp., *microbacterium* sp., etc. The extract is dissolved in a 5-10-fold volume (preferably an about 10-fold volume) of ionized water, and then it is sterilized at 121° C. for 30 minutes and cooled to 30° C. Precultured microorganisms are inoculated into the extract solution in an amount of 5-10 wt % based on the weight of the extract solution and cultured at 30° C. for 2-5 days. Then, the scavenging rate of the substrate is examined by thin layer chromatography, and when the substrate is completely eliminated, the reaction is completed, and the reaction solution is centrifuged at 5,000-10,000 rpm. The collected precipitate is washed three times with distilled water, thus obtaining a precipitate.

After the hydrolysis reaction is carried out as described above using an acid, a base, an enzyme or a microorganism producing the enzyme, the reaction solution is concentrated under reduced pressure to remove the solvent. To the residue, an alcohol selected from the group consisting of methanol, ethanol and butanol is added, and the solution is stirred 1-5 times. Then, the precipitated salts are removed by filtration, and the filtrate is concentrated under reduced pressure, thus obtaining ginsenoside F1.

The whitening cosmetic composition of the present invention contains said ginsenoside F1 in an amount of 0.0001-10 wt % based on the total weight of the composition. If the content of ginsenoside F1 is less than 0.0001 wt %, it cannot provide a whitening effect and the like, and if the content exceeds 10 wt %, the increase in the content will not lead to an increase in the effect thereof.

The whitening cosmetic composition of the present invention inhibits the production of skin melanin induced by UV light or inflammation and ameliorates pigmentation.

There is no particular limitation on the formulation of the whitening cosmetic composition of the present invention, and the inventive composition can be formulated into cosmetic products, for example, skin lotion, astringent lotion, milk lotion, nourishing cream, massage cream, essence, eye cream, eye essence, cleansing cream, cleansing foam, cleansing water, pack, powder, body lotion, body cream, body oil and body essence.

ADVANTAGEOUS EFFECTS

The ginseng-derived ginsenoside F1 (20-O-β-D-glucopyranosyl-20(S)-protopanaxatriol) which is provided according to the present invention has the effects of inhibiting melanin production and ameliorating pigmentation. Because of such effects, the ginsenoside F1 (20-O-β-D-glucopyranosyl-20(S)-protopanaxatriol) may be advantageously used in cosmetic compositions for inhibiting melanin production and ameliorating pigmentation produced by UV light.

BEST MODE

Hereinafter, the present invention will be described in further detail with reference to examples and test examples, but the scope of the present invention is not limited only to these examples.

Reference Example 1

Preparation of Ginseng Extract 2 kg of ginseng was added to 4 l of aqueous methanol solution and extracted 3 times under reflux, followed by incubation at 15° C. for 1 day. Then, the extracted plant was separated into residue and a filtrate through filter-cloth filtration and centrifugation, and the filtrate was concentrated under reduced pressure. The concentrate was suspended in water, and then extracted five times with 1 l of ethanol to remove pigments therefrom, and the aqueous layer was extracted three times with 500 ml of 1-butanol. The resulting total 1-butanol layer was concentrated under reduced pressure to obtain a 1-butanol extract which was then dissolved in a small amount of methanol and added to a large amount of ethyl acetate. The produced precipitate was dried, thus 100 g of a ginseng extract.

Example 1

Preparation of Ginsenoside F1 by Acid Hydrolysis 10 g of the ginseng extract obtained in Reference Example 1 was added to a 20-fold volume (v/w) of a 1N HCl-50% methanol solution (v/v) and hydrolyzed by heating under reflux in a water bath at 80° C. for 8 hours. Then, the reaction solution was concentrated under reduced pressure to remove the solvent, and the residue was added to 200 ml of ethanol and stirred three times. Then, the precipitated salts were removed by filtration, and the filtrate was concentrated under reduced pressure, thus obtaining a crude product. The crude product was purified by silica gel column chromatography (chloroform:methanol=8:1-4:1), thus obtaining 1.25 g of ginsenoside F1.

Example 2

Preparation of Ginsenoside F1 by Base Hydrolysis 10 g of the ginseng extract obtained in Reference Example 1 was dissolved in 500 ml of dry pyridine, and 10 g of sodium methoxide powder was added thereto. Then, the solution was hydrolyzed by heating under reflux in a water bath for 8 hours, and the reaction solution was concentrated under reduced pressure to remove the solvent. The residue was added to 200 ml of ethanol and stirred three times. The precipitated salts were removed by filtration. The filtrate was concentrated under reduced pressure, thus obtaining a crude product. The crude product was purified by silica gel column chromatography (chloroform:methanol=8:1-4:1), thus obtaining 0.85 g of ginsenoside F1.

Example 3

Preparation of Ginsenoside F1 by Enzyme Hydrolysis 10 g of the ginseng extract obtained in Reference Example 1 was dissolved in 100 ml of a 0.1M acetic acid solution (pH 4.5), and 2.5 g of enzymes (0.5 g of hesperidinase, 0.5 g of naringinase, 0.5 g of cellulose, 0.2 g of β-glucuronidase, and 0.3 g of amyloglucosidase; manufactured by Sigma) was added. Then, the solution was stirred in a water bath at 37° C. for 48 hours and heated in hot water at 80-100° C. for 10 minutes. After completion of the reaction, the reaction solution was concentrated under reduced pressure to remove the solvent, and the residue was added to 200 ml of ethanol and stirred three times. The precipitate was removed by filtration, and the filtrate was concentrated under reduced pressure, thus obtaining a crude product. The crude product was purified by silica gel column chromatography (chloroform:methanol=8:1-4:1), thus obtaining 0.91 g of ginsenoside F1.

Example 4

Preparation of Ginsenoside F1 Using Microorganisms 10 g of ginseng extract obtained in Example 1 was dissolved in 100 ml of ionized water and sterilized at 121° C. for 30 minutes, followed by cooling to 30° C. Then, precultured *Aspergillus niger* KCCM 11885 was inoculated into the extract solution in an amount of 5-10 wt % based on the weight of the extract solution and cultured at 30° C. for 5 days. Then, the elimination rate of the substrate was examined by thin layer chromatography, and when substrate was completely eliminated, the reaction was completed. The culture was centrifuged at 5,000-10,000 rpm, and the collected precipitate was washed three times with distilled water, and then centrifuged to collect the reaction solution as a precipitate. Then, the precipitate was added to 200 ml of ethanol and stirred three times. Then, the precipitate was removed by filtration, and the filtrate was concentrated under reduced pressure, thus obtaining a crude product. The crude product was purified by silica gel column chromatography (chloroform:methanol=8:1-4:1), thus obtaining 0.62 g of ginsenoside.

Test Example 1

Measurement of Melanin Production Inhibitory Effect Using Mouse Melanocytes Mouse melanocytes (Mel-Ab cells) derived from C57BL/6 mice were cultured in DMEM (Dulbecco's modified Eagle's media), containing 10% fetal bovine serum, 100 nM 2-O-tetradecanoyphorbol-13-acetate and 1 nM cholera toxin, in conditions of 37° C. and 5% $CO_2$. The cultured Mel-Ab cells were detached using 0.25% trypsin-EDTA and cultured in a 24-well plate at a concentration of $10^5$ cells/well. For 3 days from 2 days after the start of culture, 10 ppm of each of test substances (kojic acid, Reference Example 1 and Examples 1 to 4) was added to the cells being cultured. Herein, kojic acid was used as a control group in order to examine the melanin production inhibitory effect of ginsenoside F1 of the present invention.

The medium was removed, and the cells were washed with PBS and lysed with 1N sodium hydroxide. The absorbance of the cells was measured at 400 nm, and then the melanin production inhibitory rate (%) of each test sample was calculated according to the resulting equation 1. The calculation results are shown in Table 1 below (Dooley method).

Melanin production inhibitory rate (%)=100−(absorbance of each test sample/absorbance of control group×100)   [Equation 1]

TABLE 1

| Melanin production inhibitory effect | |
|---|---|
| Test samples | Melanin production inhibitory rate (%) |
| Reference Example 1 | 21.3 |
| Example 1 | 35.1 |
| Example 2 | 33.6 |
| Example 3 | 34.2 |
| Example 4 | 34.9 |
| Kojic acid | 30.5 |

As can be seen in Table 1 above, the ginsenoside F1 according to the present invention showed excellent melanin production inhibitory rate (%) compared to the existing whitening agent kojic acid. In addition, it can be seen that the melanin production inhibitory rate (%) was almost similar between the hydrolysis methods of preparing the ginsenoside F1 from the ginseng extract.

Test Example 2

Test of Whitening Effect on Human Skin

An opaque tape having a perforated hole of a 1.5 cm-diameter was attached to the upper arm of each of 12 healthy men. Then, UV rays (UVB) were irradiated to each of the subjects at a dose 1.5-2 times higher than the minimal erythema dose, thus inducing skin's blackness.

After the UV irradiation, a 1 wt % solution of each of the test samples (1,3-butyleneglycol: ethanol=7:3, as a vehicle) was applied to the skin of each subject. As negative and positive control groups, a 3 wt % solution of each of kojic acid and a vehicle was applied to the skin of each subject. A control group was not applied with anything, and a change in the state of the subject's skin was observed for 10 weeks. The skin color was measured with a colorimeter (Minolta, Japan) at a 1-week interval. Then, the difference (ΔL*) in skin color between the time point of application and the time point of completion of application of each sample was calculated according to the following equation 2, and the calculation results are shown in Table 2 below. Meanwhile, the whitening effect of each sample was evaluated by comparing ΔL* between the site applied with each sample and the control site. In the evaluation, a ΔL* value of about 2 indicates that the pigmentation is clearly ameliorated, and a ΔL* value higher than about 1.5 indicates that the sample has a whitening effect.

$$\Delta L^* = L^* \text{value at time point of completion of application} - L^* \text{value at time point of start of application} \quad \text{[Equation 2]}$$

TABLE 2

Whitening effect on human skin

| Test samples | Lightless (ΔL*) of skin color |
|---|---|
| Control group | 0.45 ± 0.13 |
| Vehicle | 0.50 ± 0.15 |
| Kojic acid | 1.56 ± 0.11 |
| Reference Example 1 | 1.26 ± 0.13 |
| Example 1 | 1.60 ± 0.13 |
| Example 2 | 1.67 ± 0.17 |
| Example 3 | 1.71 ± 0.13 |
| Example 4 | 1.64 ± 0.21 |

As can be seen in Table 2, the ginsenoside F1 according to the present invention had a ΔL value higher than 1.6, suggesting that it had an excellent whitening effect. Furthermore, it can be seen that the ginsenoside F1 according to the present invention had an excellent whitening effect compared to kojic acid known to have an excellent whitening effect.

INDUSTRIAL APPLICABILITY

As described above, the ginsenoside F1 extracted from ginseng has excellent effects of inhibiting melanin production and ameliorating pigmentation produced by UV light. Accordingly, the present invention can provide a cosmetic composition, which contains the ginsenoside F1 as an active ingredient, and thus has an excellent whitening effect.

The invention claimed is:

1. A method of whitening skin of a subject in need thereof by applying to the skin a cosmetic composition containing ginsenoside F1 (20-O-β-D-glucopyranosyl-20(S)-protopanaxatriol) as an active ingredient.

2. The method of claim 1, wherein the ginsenoside F1 is present in an amount of 0.0001-10 wt % based on the total weight of the composition.

* * * * *